(12) United States Patent
Lee

(10) Patent No.: US 7,578,604 B2
(45) Date of Patent: Aug. 25, 2009

(54) INTENSE PULSE LIGHT DEVICE HAVING INDIVIDUAL ROTATIONAL LIGHT FILTERS THEREIN

(76) Inventor: Young-Su Lee, Beoksanblooming 202-504, 334 Gocheok 1-dong, Guro-gu, Seoul (KR) 152-837

( * ) Notice: Subject to any disclaimer, the term of this patent is extended or adjusted under 35 U.S.C. 154(b) by 394 days.

(21) Appl. No.: 10/590,484

(22) PCT Filed: Apr. 2, 2004

(86) PCT No.: PCT/KR2004/000773

§ 371 (c)(1),
(2), (4) Date: Aug. 24, 2006

(87) PCT Pub. No.: WO2005/079917

PCT Pub. Date: Sep. 1, 2005

(65) Prior Publication Data

US 2008/0225524 A1 Sep. 18, 2008

(30) Foreign Application Priority Data

Feb. 25, 2004 (KR) .................. 10-2004-0012778

(51) Int. Cl.
*F21V 29/00* (2006.01)

(52) U.S. Cl. .................. 362/294; 362/373; 606/9; 607/88; 607/94; 313/22; 313/23; 313/24; 313/25; 313/26; 313/35; 313/36; 313/318.11; 601/15

(58) Field of Classification Search .......... None
See application file for complete search history.

(56) References Cited

U.S. PATENT DOCUMENTS 5,405,368 A * 4/1995 Eckhouse .............. 607/88
5,552,892 A 9/1996 Nagayama
6,214,034 B1 4/2001 Azar
6,383,177 B1 * 5/2002 Balle-Petersen et al. ....... 606/9

(Continued)

FOREIGN PATENT DOCUMENTS

WO    WO 91/15264    10/1991

*Primary Examiner*—Bao Q Truong
*Assistant Examiner*—Danielle Allen
(74) *Attorney, Agent, or Firm*—Buchanan Ingersoll & Rooney PC

(57) ABSTRACT

Disclosed is an intense pulse light device, in which plural divided light filters coated with individually different materials are rotatably and uniformly aligned around a reflection mirror in order to selectively filter lights according to wavelengths thereof, so that it is not necessary to exchange a handle body or filters, thereby improving convenience of use for the IPL device, and in which the loose contact of power lines and signal lines, leakage of cooling water, and penetration of impurities can be prevented, thereby improving reliability of IPL device. A semicircular reflection mirror aligned around a flash lamp installed in a body and a light filter section is aligned around the reflection mirror while forming a predetermined space therebetween. The light filter section is uniformly divided into two or four light filters so as to increase selectivity for the light radiated from flash lamp. The light filter section is fabricated by uniformly dividing a circular pipe made from glass, quartz or sapphire into plural pipe sections, coating the plural pipe sections with individually different materials in such a manner that only light having a predetermined wavelength passes therethrough, and bonding the plural pipe sections to each other.

7 Claims, 11 Drawing Sheets

U.S. PATENT DOCUMENTS

| | | |
|---|---|---|
| 6,461,866 B1 | 10/2002 | Whitehurst |
| 6,613,040 B2 | 9/2003 | Tankovich et al. |
| 7,097,639 B1 * | 8/2006 | Almeida ........................ 606/9 |
| 2001/0029364 A1 * | 10/2001 | Almeida ........................ 606/9 |
| 2002/0183811 A1 * | 12/2002 | Irwin ........................ 607/94 |
| 2003/0004499 A1 | 1/2003 | McDaniel |

* cited by examiner

Circular pipe → Division of circular pipe → Coating A → Coating B → Coating C → Coating D → Coating A, B, C, D bonding Light path Light path

INTENSE PULSE LIGHT DEVICE HAVING INDIVIDUAL ROTATIONAL LIGHT FILTERS THEREIN

TECHNICAL FIELD

The present invention relates to an intense pulse light (IPL) device used for caring a skin, and more particularly to an IPL device, in which plural divided light filters coated with individually different materials are rotatably and uniformly aligned around a reflection mirror in order to selectively filter lights according to their wavelengths, so that it is not necessary to exchange a handle body or filters, thereby improving convenience of use for the IPL device, and in, which the loose contact of power lines and signal lines, leakage of cooling water, and penetration of impurities can be prevented, thereby improving reliability of the IPL device.

The present invention also relates to a method for exchanging a rotational light filter of an IPL device adaptable for caring a skin with superior reliability by preventing the loose contact of power lines and signal lines, leakage of cooling water, and penetration of impurities.

BACKGROUND ART

A conventional IPL device used for caring a skin includes a main instrument, a foot switch used for controlling irradiation of light, and a handle. The main instrument has an automatic control panel, a power source and a cooling system. In order to exchange a filter accommodated in the handle of the IPL device, a handle bundle or an auxiliary filter must be exchanged.

However, according to the conventional filter exchange scheme, the light filters must be mechanically or electrically rotated in order to exchange the handle bundle or the auxiliary filter, causing inconvenience of filter exchange work. In addition, the loose contact of power lines and signal lines, leakage of cooling water, and penetration of impurities may occur after the filter exchange work has been completed.

FIGS. 5a and 5b show a conventional IPL device 10.

Referring to FIG. 5A, the conventional IPL device 10 mainly includes a body 11, a plurality of optical tube connectors 12a and 12b detachably coupled to the body 11, a plurality of cooling water circulation pipes 13 extending by passing through the body 11 and the optical tube connectors 12a and 12b, and an electric cable 14 extending between the body 11 and an external power source.

Referring to FIG. 5B, a primary optical tube 21 and a secondary optical tube 22 are installed in the optical tube connectors 12a and 12b and the body 11. That is, the primary optical tube 21 and the secondary optical tube 22 are accommodated in the optical tube connectors 12a and 12b, which are coupled with each other by means of a plurality of bolts and nuts, and fixedly inserted to the body 11.

FIG. 6A is a schematic view illustrating an internal structure of the conventional IPL device.

Referring to FIG. 6A, a pipe-shaped flash lamp 15, which is a light source, is longitudinally aligned in the body 11. In addition, the cooling water circulation pipe 13 is aligned around the flash lamp 15 in order to cool the flash lamp 15, and a semicircular reflection mirror 16 is aligned around the cooling water circulation pipe 13.

An optical tube assembly 20 is disposed below the flash lamp 15 in the body 11 of the IPL device 10 (see FIG. 6 so as to emit the light radiated from the flash lamp 15 to the exterior.

FIG. 6B is a schematic view illustrating a structure of the optical tube assembly of the conventional IPL device.

Referring to FIG. 6B, the optical tube assembly 20 includes the primary optical tube 21, the secondary optical tube 22, and a TEM 23, which is a thermoelectric module capable of cooling the primary and secondary optical tubes 21 and 22. Light radiated from the flash lamp 15 installed in the body 11 is emitted to the exterior vertically to the body 11 through the primary aid secondary optical tubes 21 and 22. The light emitted to the exterior radiates onto the skin of the patient through the secondary optical tube 22, which is aligned adjacent to the skin of the patient.

The conventional IPL device 10 having the above construction can radiate lights having various wavelengths, such as 560 to 1200 nm (for skin care), 590 to 1200 nm (for vascular lesion), 640 to 1200 nm (for hair removal), and 700 to 1200 nm (for hair removal), according to the purpose of the skin care. In addition, the optical tube assembly 20 must be disassembled from or reassembled into the body according to the purpose of the skin care.

Therefore, not only it is inconvenient to use the conventional IPL device, but also the loose contact of the power line or the signal line, leakage of cooling water and penetration of impurities may occur.

FIG. 7A is a schematic view illustrating a structure of an optical tube assembly of another conventional IPL device.

The optical tube assembly 30 shown in FIG. 7A is similar to the optical tube assembly 20 shown in FIG. 6B except that the optical tube assembly 30 shown in FIG. 7A has a primary optical tube 31 larger than a secondary optical tube 32 and the secondary optical tube 32 is detachably coupled to a lower portion of the primary optical tube 31.

The optical tube assembly 30 includes a primary optical tube 31, a secondary optical tube 32, and a TEM 33, which is a thermoelectric module capable of cooling the primary and secondary optical tubes 31 and 32. Light radiated from the flash lamp 15 installed in the body 11 is emitted to the exterior vertically to the body 11 through the primary and secondary optical tubes 31 and 32. The light emitted to the exterior is radiated onto a skin of a patient through the secondary optical tube 32, which is aligned adjacent to the skin of the patient.

FIG. 7B is a schematic view illustrating a structure of the IPL device having the optical tube assembly 30 as shown in FIG. 7A.

As shown in FIG. 7B, the secondary optical tube 32 of the optical tube assembly 30 is slidably and detachably installed in a filter guide holder 34, which is integrally formed with lower portions of the optical tube connectors 12a and 12b.

In the conventional IPL device 10 having the above construction, the secondary optical tube 32, which is a main filter, is slidably exchanged. However, impurities may penetrate into the IPL device 10 or the filter may be damaged when the filter has been exchanged. In this case, it is impossible to normally perform the skin care.

DISCLOSURE OF THE INVENTION

Therefore, the present invention has been made in view of the above-mentioned problems, and it is an object of the present invention to provide an IPL device used for caring a skin, in which wavelength-selective filters are rotatably installed, thereby improving convenience of use for the IPL device, and in which the loose contact of power lines and signal lines, leakage of cooling water, and penetration of impurities can be prevented.

In order to accomplish the above object, there is provided an IPL device comprising: a body; a flash lamp having a pipe shape and being installed in the body, a cooling water circulation pipe aligned around the flash lamp, a semicircular reflection mirror aligned at an outer portion of the cooling water circulation pipe; an optical tube assembly installed in the body in order to emit light radiated from the flash lamp to an exterior; and a light filter section aligned around the reflection mirror while forming a predetermined space therebetween.

According to the preferred embodiment of the present invention, the light filter section is uniformly divided into plural light filters so as to increase selectivity for the light radiated from the flash lamp.

The light filter section is rotatable with respect to the flash lamp and is uniformly divided into two or four light filters.

The light filter section is fabricated by uniformly dividing a circular pipe into plural pipe sections, coating the plural pipe sections with individually different materials in such a manner that only light having a predetermined wavelength passes therethrough, and bonding the plural pipe sections to each other.

In the above IPL device, plural divided light filters coated with individually different materials are rotatably and uniformly aligned around a reflection mirror in order to selectively filter lights according to wavelengths thereof, so that it is not necessary to exchange a handle body or filters, thereby improving convenience of use for the IPL device. In addition, the loose contact of power lines and signal lines, leakage of cooling water, and penetration of impurities can be prevented, thereby improving reliability of the IPL device.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Hereinafter, an IPL device according to a preferred embodiment of the present invention will be described with reference to accompanying drawings.

Figure 1:
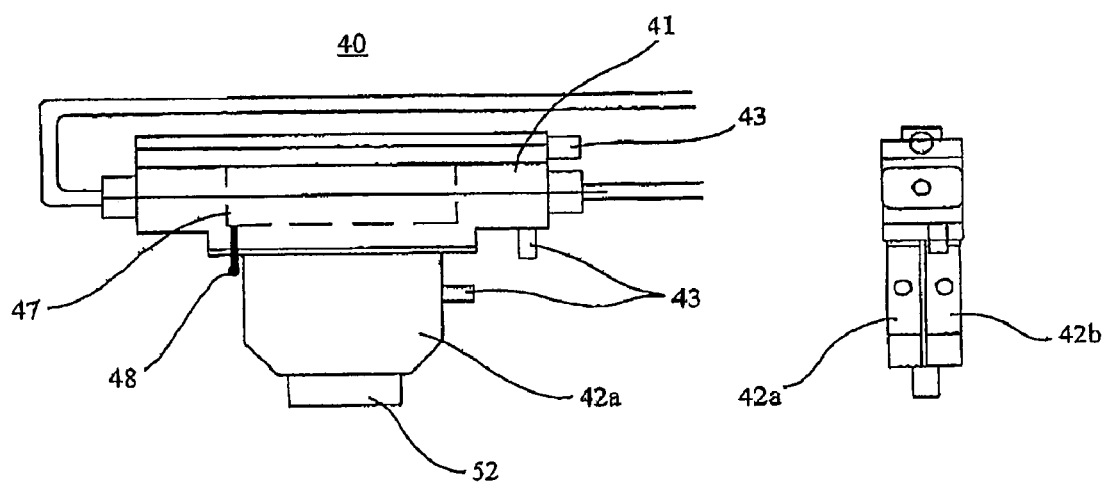
FIG. 1 is a schematic view of an IPL device according to one embodiment of the present invention.

FIG. 1 is a schematic view of an IPL device according to one embodiment of the present invention.

Referring to FIG. 1, the IPL device 40 according to the present invention mainly includes a body 41, a plurality of optical tube supporters 42a and 42b detachably coupled to the body 41, a plurality of cooling water circulation pipes 43 extending by passing through the body 41 and the optical tube supporters 42a and 42b, and an electric cable (not shown) extending between the body 41 and an external power source.

Figure 2A:
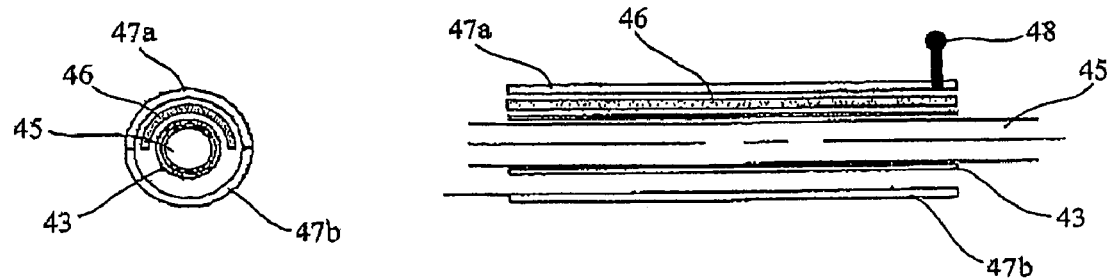
FIG. 2A is a schematic view illustrating an internal structure of an IPL device according to one embodiment of the present invention.

FIG. 2A is a schematic view illustrating an internal structure of the IPL device 40 according to the present invention.

Referring to FIG. 2A, a pipe-shaped flash lamp 45, which is a light source, is longitudinally aligned in the body 41 of the IPL device 40, the cooling water circulation pipe 43 is aligned around the flash lamp 45 in order to cool the flash lamp 45, and a semicircular reflection mirror 46 is aligned at a radially outer portion of the cooling water circulation pipe 43. In addition, a pair of rotational light filters 47a and 47b having semicircular shapes are aligned around a reflection mirror 46. A rotating stick 48 is integrally formed with the rotational light filters 47a and 47b in order to rotate the rotational light filters 47a and 47b.

Figure 3:
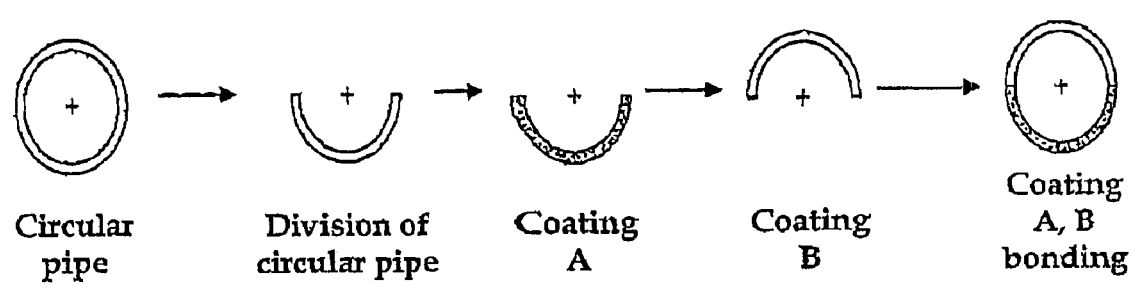
FIG. 3 is a view illustrating a procedure for manufacturing a filter section according to one embodiment of the present invention.

FIG. 3 is a view illustrating a procedure for manufacturing the rotational light filters 47a and 47b shown in FIG. 2A.

Referring to FIG. 3, differently from the conventional filter capable of filtering only one wavelength, the rotational light filters 47a and 47b can selectively filter multiple wavelengths. To his end, as shown in FIG. 3, a circular pipe made from glass, quartz or sapphire is uniformly divided into two pipe sections. The two pipe sections are coated with individually different materials in such a manner that only light having a predetermined wavelength may pass therethrough. Then, the two pipe sections are bonded to each other.

Figure 4:
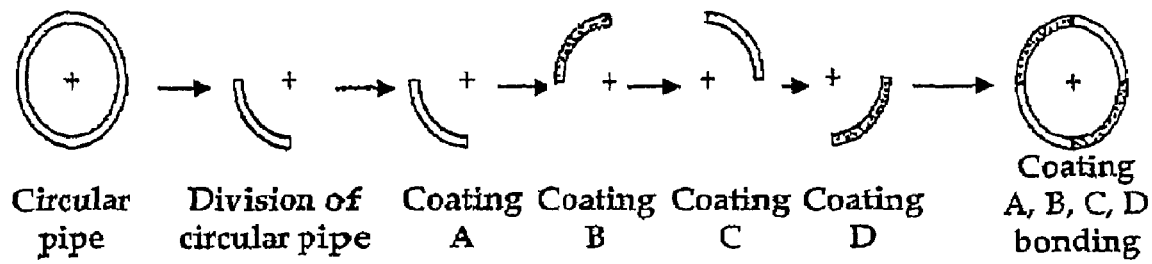
FIG. 4 is a view illustrating a procedure for manufacturing a filter section according to another embodiment of the present invention.
Figure 5A:
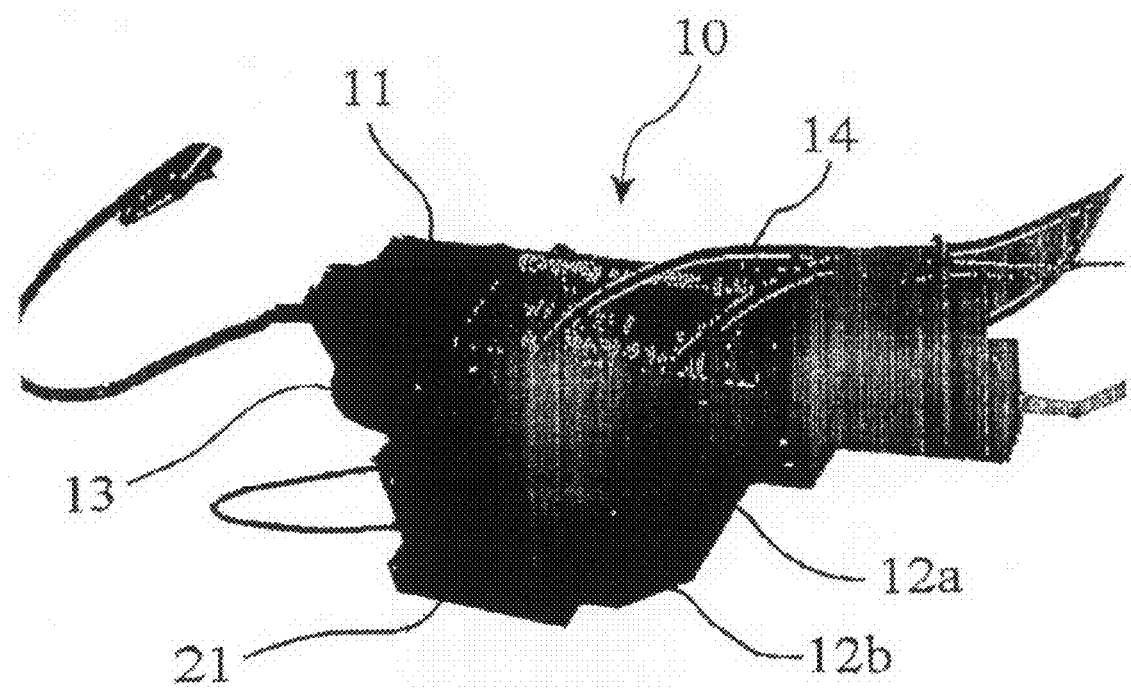
FIGS. 5A and 5B are views illustrating conventional IPL devices, respectively.
Figure 5B:
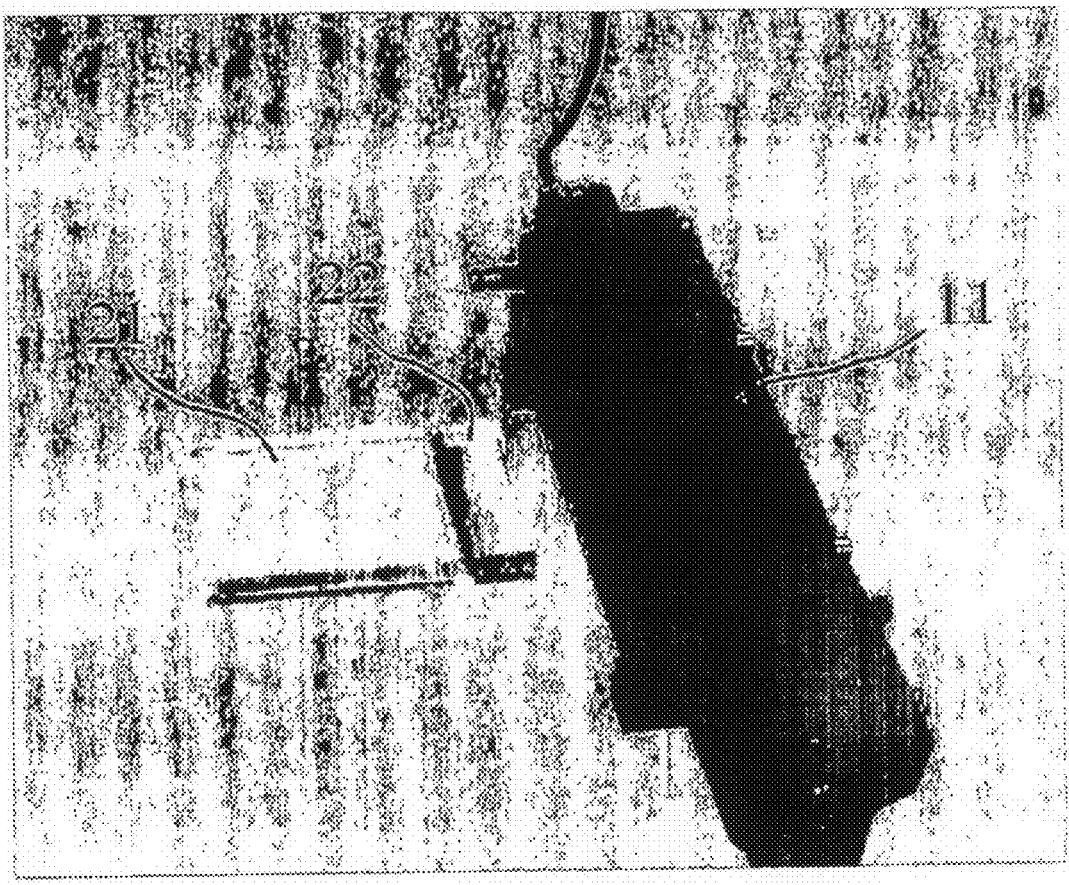
Figure 6A:
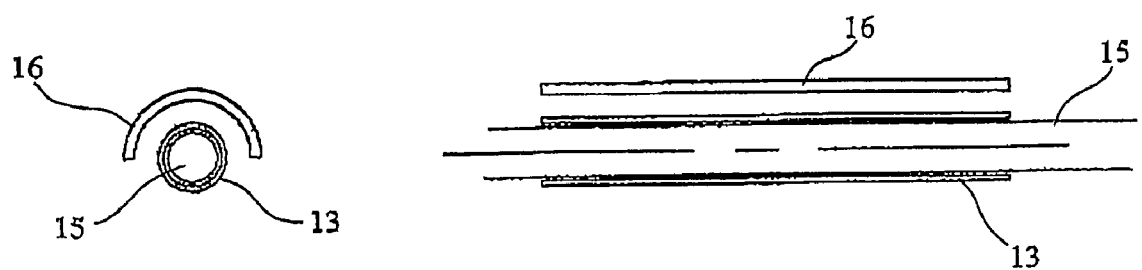
FIG. 6A is a view illustrating an internal structure of a conventional IPL device.
Figure 6B:
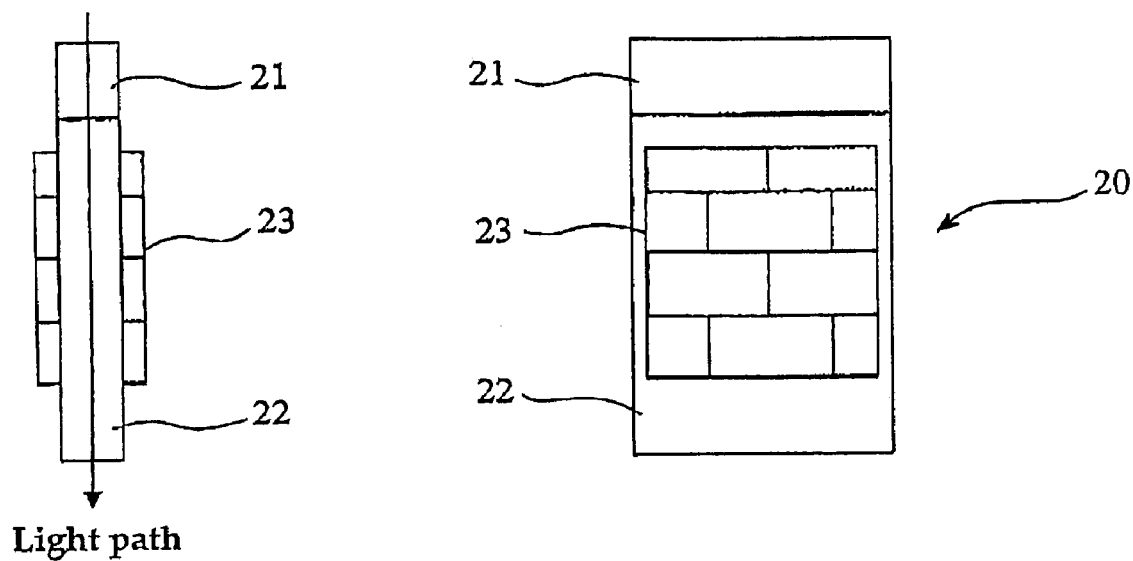
FIG. 6B is a view illustrating a structure of au optical tube assembly of a conventional IPL device.
Figure 7A:
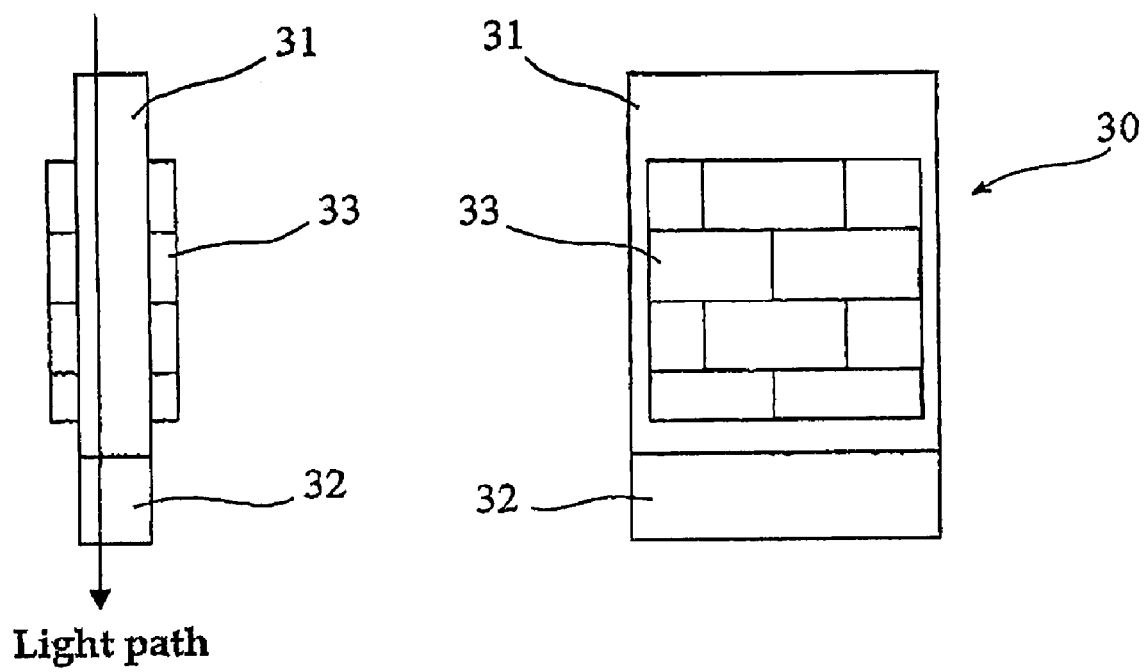
FIG. 7A is a view illustrating a structure of an optical tube assembly of another conventional IPL device.
Figure 7B:
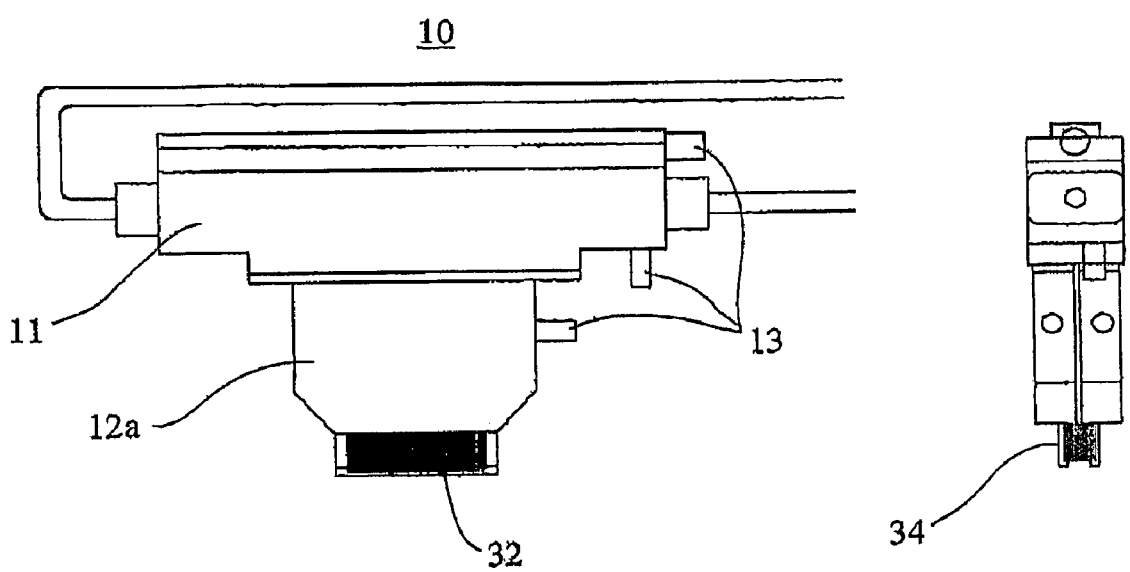
FIG. 7B is a view illustrating the structure of an IPL device shown in FIG. 7A.

FIG. 4 is a view illustrating a procedure for manufacturing a filter section according to another embodiment of the present invention.

Referring to FIG. 4, differently from the filter section shown in FIG. 3, which is divided into the light filters 47a and 47b, the filter section shown FIG. 4 is divided into foul light filters in order to increase selectivity for wavelengths of the light. To this end, as shown in FIG. 4, a circular pipe made from glass, quartz or sapphire is uniformly divided into four pipe sections. The four pipe sections are coated with individually different materials in such a manner that only light having a predetermined wavelength may pass therethrough. Then, the four pipe sections are bonded to each other.

Although FIGS. 3 and 4 show the filter section divided into two light filters and four light filters, respectively, it can be easily understood to those skilled in the art 10 that the filter section can be divided into six light filters, eight filters or twelve filters.

In addition, an optical tube assembly 50 is aligned below the flash lamp 45 installed in the body 41 of the IPL device 40 in order to emit the light radiated from the flash lamp 45 to the exterior.

Figure 2B:
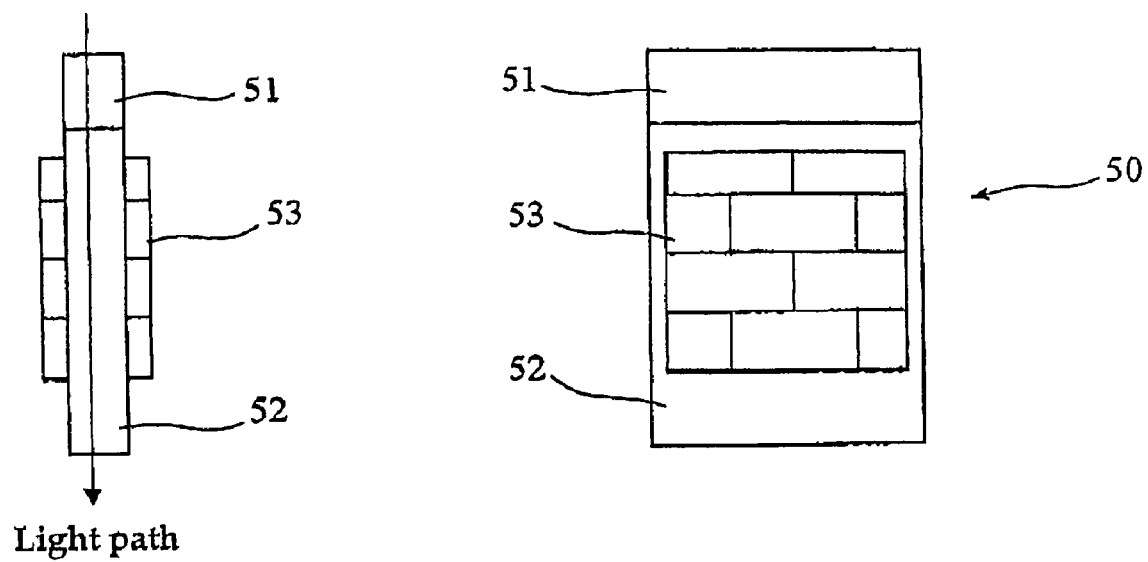
FIG. 2B is a schematic view illustrating a structure of an optical tube assembly of an IPL device according to one embodiment of the present invention.

FIG. 2B is a schematic view illustrating a structure of an optical tube assembly of an IPL device according to one embodiment of the present invention.

Referring to FIG. 2B, the optical tube assembly 50 includes a primary optical tube 51, a secondary optical tube 52, and a TEM 53, which is a thermoelectric module capable of cooling the primary and secondary optical tubes 51 and 52. Light radiated from a flash lamp 55 installed in the body 41 is introduced towards the primary and secondary optical tubes 51 and 52 through a semicircular reflection mirror 46.

At this time, the light is divided according to the wavelength thereof while passing through the rotational light filters 47a and 47b coated with individually different materials. That is, after dividing the light based on the wavelength thereof by rotating the rotational light filters 47a and 47b using the rotating stick 48 integrally coupled with the rotational light filters 47a and 47b, the light is emitted to the exterior vertically to the body 41 through the primary and secondary optical tubes 51 and 52. The light emitted to the exterior is radiated onto a skin of a patient through the secondary optical tube 52, which is aligned adjacent to the skin of the patient.

INDUSTRIAL APPLICABILITY

As can be seen from the foregoing, according to the IPL device of the present invention, plural divided light filters coated with individually different materials are rotatably and uniformly aligned around the reflection mirror in order to selectively filter lights according to wavelengths thereof, so that it is not necessary to exchange a handle body or filters, thereby improving convenience of use for the IPL device. In addition, the loose contact of power lines and signal lines, leakage of cooling water, and penetration of impurities can be prevented, thereby improving reliability of the IPL device.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. An intense pulse light device comprising:
   a body;
   a flash lamp having a pipe shape and being installed in the body;
   a cooling water circulation pipe aligned around the flash lamp;
   a semicircular reflection mirror aligned at an outer portion of the cooling water circulation pipe;
   an optical tube assembly installed in the body in order to emit light radiated from the flash lamp to an exterior; and
   a light filter section aligned around the reflection mirror while forming a predetermined space therebetween;
   wherein the flash lamp and the light filter section are relatively rotatable.

2. The intense pulse light device as claimed in claim 1, wherein the light filter section is uniformly divided into plural light filters so as to increase selectivity for the light radiated from the flash lamp.

3. The intense pulse light device as claimed in claim 2, wherein the light filter section is rotatably with respect to the flash lamp and is uniformly divided into two light filters.

4. The intense pulse light device as claimed in claim 2, wherein the light filter section is rotatably with rospoct to tho flash lamp and is uniformly divided into four light filters.

5. The intense pulse light device as claimed in claim 3, wherein the light filter section comprises a uniformly divided circular pipe defining a plurality of pipe sections, each of the pipe sections are coated with individually different materials in such a manner that only light having a predetermined wavelength passes therethrough.

6. The intense pulse light device as claimed in claim 4, wherein the light filter section comprises a uniformly divided circular pipe defining a plurality of pipe sections, each of the plural pipe sections are coated with individually different materials in such a manner that only light having a predetermined wavelength passes therethrough.

7. The intense pulse light device as claimed in claim 1, further comprising a rotating stick operatively associated with the light filter section.

\* \* \* \* \*